(12) United States Patent
Laforét

(10) Patent No.: US 6,395,261 B1
(45) Date of Patent: May 28, 2002

(54) WALNUT SEED MEAL EXTRACT

(75) Inventor: Jean-Pierre Laforét, Genas (FR)

(73) Assignee: Gattefosse S.A., Saint Priest (FR)

( * ) Notice: Subject to any disclaimer, the term of this patent is extended or adjusted under 35 U.S.C. 154(b) by 0 days.

(21) Appl. No.: 09/866,433

(22) Filed: May 25, 2001

Related U.S. Application Data

(63) Continuation of application No. PCT/FR99/02925, filed on Nov. 26, 1999.

(30) Foreign Application Priority Data

Nov. 27, 1998 (FR) .............................. 98 15162

(51) Int. Cl.⁷ .......................... A61K 7/42; A61K 7/44; A61K 7/00; A61K 35/78
(52) U.S. Cl. .......................... 424/59; 424/60; 424/400; 424/401; 424/725; 424/771
(58) Field of Search ............................ 424/59, 60, 400, 424/401, 725, 771

(56) References Cited

U.S. PATENT DOCUMENTS 5,137,717 A    8/1992   Wixforth .................. 424/78.07

FOREIGN PATENT DOCUMENTS

| EP | 0306853 | 9/1988 | ............ A61K/7/26 |
| FR | 72.41929 | 11/1972 | |
| GB | 673501 | 6/1952 | |
| WO | 91/11169 | 8/1991 | ............ A61K/7/48 |

OTHER PUBLICATIONS

Alary "The walnut (Juglans regia), its oil, and its oil cake" Chem. Abstr. 103:21432.

*Primary Examiner*—Shelley A. Dodson
(74) *Attorney, Agent, or Firm*—Heslin Rothenberg Farley & Mesiti P.C.

(57) ABSTRACT

An aqueous extract of walnut seed meal useful in cosmetic and dermatologic compositions is disclosed. The extract is obtained by macerating the pressed seed meal from Juglans sp. in water and concentrating the water.

23 Claims, No Drawings

WALNUT SEED MEAL EXTRACT

CROSS REFERENCE TO RELATED APPLICATIONS

This application is a continuation of PCT application PCT/FR99/02925 filed Nov. 26, 1999, and published in French as WO 00/32163 on Jun. 8, 2000. PCT/FR99/02925 claimed the priority of British application FR/98.15162, filed Nov. 27, 1998. The entire disclosures of both are incorporated herein by reference.

The invention relates to a walnut seed cake extract. It also relates to a cosmetic composition comprising said extract. Its subject is also various applications of the extract and therefore of the cosmetic composition.

In the remainder of the description and in the claims, "walnut seed cake" designates the residue from the pressing of walnut seed after extraction of the oil which it contains, commonly called "walnut oil".

Walnut trees belonging to the Juglandaceae family are widely distributed and cultivated in temperate countries. This includes in particular *Juglans regia* which is found in Europe or *Juglans regia* which is found in America, which are the subject of a number of applications.

There has thus been described, in the document RO-A-103 270, a cosmetic composition used for washing hair and comprising, in combination, a salicylate and an alcoholic extract of walnut tree of the *Juglans regia* type. However, nothing is indicated regarding the part of the tree from which the extract is obtained.

There has also been described, in the document EP-A-0306853, a cosmetic composition exhibiting germicidal properties, containing extracts of barks of roots of trees of the Juglandaceae family.

Likewise, certain parts of the walnut have been identified as having advantageous properties.

This is for example the case for the walnut hull constituting the outer fleshy part of the walnut, which contains a naphthoquinone compound (juglone) used as hair dye.

On the other hand, the residue from the pressing of the walnut seed constituting the cake has never been upgraded and has consequently not received any particular application.

The Applicant has sought to isolate a walnut seed cake extract and has observed that it exhibits a number of advantageous properties.

The invention therefore relates to a seed cake extract of walnuts produced by a walnut tree of the genus *Juglans* which can be obtained by a step of aqueous extraction of the cake followed by a concentration step.

Advantageously, the concentration is carried out by reverse osmosis.

The preparation of an aqueous extract can be accomplished by any of the techniques known to persons of skill in the art, including maceration, percolation, digestion, microwave, and ultrasonic waves. The temperature can vary depending on the process. Indeed, the extraction can be conducted at ambient or higher temperature, although high temperatures and long exposure times will result in partial destruction of active ingredients. The period of contact may vary depending on which extraction process is used. If the extraction is conducted using microwaves and the weight of seed cake is small in comparison to the power of the microwave, the period of contact can be as short as a few seconds. There is an inverse relationship between time and temperature. The ratio of walnut seed cake to solvent (water) is a balance between the amount of solvent needed for efficient extraction and the amount of solvent that must be subsequently removed. Typical reasonable ratios fall between 1/99 and 20/80 (by weight). Ratios falling outside this range will work, but they sacrifice process efficiency. We have found that 5:95 is a good ratio. The optimal extraction process is maceration, carried out at a temperature between 3 and 10° C., advantageously at about 4° C. A temperature less than 3° C. may cause the formation of ice; a temperature greater than 10° C. risks causing a decline in the activity of the extract. When the extraction process is maceration at 3 to 10° C. for less than 40 hours, exposure time determines only the efficiency of the extraction, not the nature of the extract. We have found that about 20 hours is optimal.

The extract obtained is provided in the form of a concentrated aqueous solution.

To obtain the extract in powdered form, the concentration step is followed by a drying or freeze-drying step.

Advantageously, the walnuts from which the cake extract is derived are produced by a walnut tree (Jugans regia).

As already stated, the walnut cake extract of the invention has a number of advantageous properties, such that it can be used for various applications, in particular in cosmetic compositions.

1/Protective Activity of the Walnut Seed Cake Extract Toward the Intracellular Oxidation Caused by an Oxidative Stress of the UVB Type The experimental approach used for this evaluation is based on the measurement of the intracellular oxidation level, after exposure to LVB radiation, of human keratinocytes cultured in the absence and in the presence of the extract of the invention.

Methods

Normal human keratinocytes isolated from foreskins obtained during surgical operations are cultured in "serum-free" KGM medium at 37° C., in a humid air-$CO_2$ (95–5%) atmosphere.

After cytotoxicity studies, three concentrations of extract were selected for evaluation: 10 µg/ml, 100 µg/ml, 250 µg/ml.

Principle of the Test

The principle of the test is based on the measurement of the degree of intracellular oxidation with the aid of a specific probe: DCFH-DA (2',7'-trichlorodihydrofluorescein diacetate).

DCFH-DA, a nonfluorescent probe, penetrates by passive diffusion into the cells. After cleavage of the acetate groups by intracellular esterases, DCFH accumulates in the cytosol. The intracellular oxidation of DCFH by various Reactive Oxygen Species (ROS) leads to the formation of a fluorescent product.

The measurement of the fluorescence intensities makes it possible to evaluate the degree of oxidation of the cells subjected to an oxidative stress.

After having been detached from their support, the suspensions of keratinocytes are inoculated into 24-well plates. The cells are incubated at 37° C. for 24 hours with the medium containing the extract to be studied.

After incubation with the various concentrations of extract to be tested, the cultures are rinsed with a PBS solution and then exposed to UVB radiation, through a PBS solution.

After irradiation of the cells, the PBS solution is replaced with a solution of DCFH-DA. After incubation of the fluorescent probe, the cellular lawns are abundantly rinsed with PBS and the cells are then reincubated at 37° C. for 24 hours with fresh culture medium.

At the end of the assay, the suspended keratinocytes are transferred into thermostatted vessels and the fluorescence intensities (Abs=502 nm, Em=520 nm) are measured and expressed in percentage relative to the nonirradiated control cultures.

The results are expressed in the following table:

|  | Degree of oxidation | Protective activity |
|---|---|---|
| Control |  |  |
| no UV | 100 | — |
| 25 mJ/cm$^2$ | 144 | — |
| 50 mJ/cm$^2$ | 176 | — |
| 10 µg/ml |  |  |
| no UV | 100 | — |
| 25 mJ/cm$^2$ | 116 | 39 |
| 50 mJ/cm$^2$ | 125 | 65 |
| 100 µg/ml |  |  |
| no UV | 100 | — |
| 25 mJ/cm$^2$ | 107 | 74 |
| 50 mJ/cm$^2$ | 115 | 79 |
| 250 µg/ml |  |  |
| no UV | 100 | — |
| 25 mJ/cm$^2$ | 98 | 104 |
| 50 mJ/cm$^2$ | 106 | 92 |

Under the conditions of this study, the extract of the invention protects in a dose-dependent manner the cell against oxidative stress induced by UVB irradiation. The extract is therefore capable of regulating the level of reactive oxygen species (ROS) which form. The extract possesses the capacity to protect the cell from oxidative stress, that is to say to block the formation of ROS and/or to inhibit their reactivity by a "trapping" process.

In a first application, the extract of the invention may therefore be used to protect skin cells from oxidative stress induced by UVB irradiation.

2/Activity for Protecting Cells Against Apoptosis Induced by UVB Radiation

ROSs capable of reacting directly with DNA can introduce into this constituent multiple chemical modifications. These modifications, which have the consequence of disrupting the genetic program of the cell, are as a whole corrected by so-called repair enzymes.

However, when this repair is not complete, the cell enters into a program of programmed cell death or apoptosis leading to their elimination.

Evaluation of the Activity for Protecting Cells Against Apoptosis Induced by UVB Radiation This protective power against apoptosis induced by TVB radiation was evaluated on monolayer keratinocyte cultures by determining the percentage of apoptotic cells by means of the APOPTAG® kit (semi quantitative test).

Method

The keratinocytes are obtained from primary cultures of foreskins and are allowed to proliferate in a "serum-free" conditioned medium (KGM).

After having been detached from their support, the suspensions of keratinocytes are cultured in 24-well plates. The cells are cultured in Iscove medium supplemented with antibiotics and fetal calf serum (5%). They are exposed to the extract of the invention for 24 hours at two concentrations (10 and 100 µg/ml), and then stimulated by UVB radiation.

The number of apoptotic cells is determined 72 hours after irradiation in treated and untreated media using the APOPTAG® kit. The DNA breaks are visualized by fluorescence emission. The number of cells undergoing apoptosis is evaluated by counting the number of fluorescent cells out of a total of 200 cells.

The percentage reduction in apoptotic cells under the action of the extract of the invention is determined.

The results are expressed in the following table.

| Extract of the invention (µg/ml) | Percentage of apoptotic cells induced by UV radiation |
|---|---|
| 0 | 70 |
| 10 | 55 |
| 100 | 49.5 |

Under the influence of the extract of the invention, the amount of apoptotic cells generated by UV radiation (70%) is reduced in a dose-dependent manner.

The results of this study demonstrate that the extract of the invention possesses antiapoptotic properties at low concentrations, resulting from its capacity to limit the formation and/or the action of ROSs.

3/Anti-inflammatory Activity of the Walnut Seed Cake Extract of the Invention

In vivo, environmental stress and in particular UV radiation, by stimulating the formation of free radicals, promote the expression of numerous epidermal mediators capable of determining the development of an inflammation.

The Applicant has observed that the walnut seed cake extract was effective for limiting the development of the inflammatory reaction.

This activity was evaluated in vitro on keratinocytes and macrophages.

The keratinocytes are obtained from primary cultures of foreskins and are allowed to proliferate in a conditioned medium for two weeks. At the end of this period, the keratinocytes are cultured in 24-well plates.

The macrophages are obtained from blood samples after centrifugation. After the usual treatment, they are allowed to adhere to the Petri dish.

The extract of the invention is tested at a defined concentration. A batch of control culture, not treated with the extract of the invention, is performed in parallel.

The keratinocytes and macrophages obtained are then subjected to the following two stimuli.

The first stimulus consists in triggering a specific inflammatory reaction by activating the keratinocytes and macrophages by $IL_4$ (10 nanograms per milliliter) for 48 hours, so as to induce the production of CD23 (receptor with low affinity for IgE), which are then activated with the IgE-containing immune complexes.

The second stimulus consists in triggering, in the cells, a nonspecific inflammatory reaction by activating the keratinocytes and macrophages with a mixture of IFNγ(1000 units per milliliter) and of extract of lipopolysaccharide LPS (10 micrograms per milliliter).

The cells thus stimulated are maintained in culture for 48 hours before removing the supernatants, which are then tested by colorimetry or the ELISA method to determine their respective contents of nitro (NO) derivatives and of TNFα, constituting the pro-inflammatory mediators.

The results of the test are presented in the table below.

|  |  | TNFα (pg/ml) | NO (µM) |
|---|---|---|---|
| Stimulation with IgEs ($IL_4$) | | | |
| Keratinocytes | Control | 275 ± 16 | 9 ± 2 |
|  | Extract of the invention |  |  |
|  | (1/100 V/V) | 102 ± 11 | 0.5 ± 0.1 |
| Macrophages | Control | 985 ± 85 | 5 ± 1 |
|  | Extract of the invention |  |  |
|  | (1/100 V/V) | 125 ± 15 | not detectable |
| Stimulation with IFNγ/LPS | | | |
| Keratinocytes | Control | 775 ± 45 | 19 ± 3 |
|  | Extract of the invention |  |  |
|  | (1/100 V/V) | 302 ± 17 | 2.4 ± 0.8 |

The results of this test demonstrate the capacity of the extract of the invention to modulate the release of the proinflammatory mediators in response to various stimuli.

Indeed, in the case of inflammation dependent on IgE, triggered by $IL_4$, the extract of the invention exhibits anti-inflammatory activity on the keratinocytes (reduction of the synthesis of NO and of TNFα). An enhanced activity of the same type is noted on the macrophages.

In the case of nonspecific inflammation triggered by the IFNγ/LPS combination, only the keratinocytes are capable of producing both TNFα and nitro derivatives. In this specific case, the extract of the invention also exhibits a significant anti-inflammatory activity.

The extract of the invention may be advantageously incorporated into cosmetic compositions intended to be applied to sensitive skins, which are hyper reactive skins which are therefore very receptive to environmental stress such as UV radiation, irritant chemical agents, heat shock, pollution, allergenic agents and the like.

In this case, it will be possible to protect the skin from any environmental stress and in particular from UV radiation according to a method consisting in applying to the skin an effective quantity of the extract of the invention or of a composition comprising said extract.

The extract of the invention may also be incorporated into cosmetic compositions having an irritant potential such as those comprising surfactants or α-hydroxy acids, so as to limit the impact of certain pro inflammatory reactions linked to these components.

4/Anti Age Activity of the Walnut Seed Cake Extract of the Invention Toward the Skin It was also observed that the walnut seed cake extract of the invention was effective in combating skin ageing by virtue of its:

stimulatory activity on protein synthesis in the keratinocytes of the epidermis and fibroblasts of the dermis;
anti collagenase activity;
antielastase activity.

The extract can therefore be used in cosmetic compositions intended for combating skin ageing.

Skin ageing results from a programmed senescence leading to atrophy of the skin tissue, which appears particularly pronounced in the dermis. This atrophy results from a slowing down in cell metabolism and is responsible for the appearance in particular of wrinkles.

The dermis is a connective tissue composed of an extracellular matrix ECM) synthesized by the fibroblasts. The ECM, which is responsible for the mechanical properties of the skin, consists of various proteins, including collagen (type I and type III), elastin and glycosaminoglycans (essentially hyaluronic acid and dermatan sulfate).

Both qualitative and quantitative impairment of the extracellular matrix occur over time. This impairment results in degeneration of the collagen network, of the elastin network and in a decrease in the content of glycosaminoglycans and more particularly of hyaluronic acid. These modifications result both from a decrease in the capacity of the fibroblasts to synthesize the extracellular matrix and from a disequilibrium in the expression of certain proteinases, in particular the proteinases called Matrix Metallo proteinases and the proteinases called Tissue Inhibitor Metallo proteinases.

In this way, during ageing, the mechanical properties of the skin regress and a decrease in the tensile force or in stiffness (loss of the collagen network), and a decrease in elasticity and resilience (degeneration of the elastin network) are observed, the whole accompanied by a collapse in hydration (decrease in the hyaluronic acid level) responsible for a loss of skin turgescence.

Tests were carried out to demonstrate the anti-age activity of the extract of the invention toward the skin.
Stimulatory Activity of the Extract of the Invention on Protein Synthesis in the Keratinocytes of the Epidermis and the Fibroblasts of the Human Dermis
  a)Cytotoxicity A cytotoxicity trial was first of all carried out for the extract of the invention on fibroblasts to determine the maximum dose of extract which does not cause cytotoxicity.

Cell viability is evaluated, at the end of the trial, by a calorimetric test with MTT. The principle of this test results from the conversion, by mitochondrial succinyl dehydrogenase of metabolically active cells, of 3-(4,5-dimethylthiazol- 2-yl)-2,5-diphenyltetrazolium bromide (soluble substrate which is yellow in the oxidized state) to violet-blue formazan. The optical density of the violet-blue solution obtained at the end of the trial is proportional to the number of living cells.

The cytotoxicity of the extract of the invention was evaluated using nine different concentrations of extract of between 0.01 and 10 mg/ml. A first evaluation was carried out after 24 hours.

A second evaluation was carried out after 48 hours on concentrations of between 0.05 and 5 mg/ml.

The results are presented in the table below.

| Concentration mg/ml | 0.1 | 0.25 | 0.5 | 0.75 | 1 | 2.5 | 5 | 10 |
|---|---|---|---|---|---|---|---|---|
| Viability (24 h) | 108% | not determined | 112% | not determined | 107% | Not determined | 80% | 68% |
| Viability (48h) | 110% | 109% | 107% | 99% | 94% | 77% | 53% | not determined |

After 24 hours of contact, the concentrations of extract of less than or equal to 1 mg/ml induced no significant decrease in cell response toward MTT. Likewise, the results after 48 hours confirm the nontoxicity of concentrations of less than or equal to 1 mg/ml. Accordingly, the concentration of walnut seed cake extract of 1 mg/ml was selected as maximum noncytotoxic dose for the remainder of this study.

b) Study on the Keratinocytes of the Epidermis

Keratinocytes are cultured in monolayers. At D-1, the keratinocytes are detached from their support by gentle trypsinization. After centrifugation, the cells are resuspended in an optimum culture medium. The cellular suspensions are then inoculated.

24 hours after inoculation ($D_0$), the culture media are removed and replaced with a different medium containing various concentrations of walnut seed cake extract.

Once treated, the keratinocytes are again placed in the oven at 37° C. and incubated for 72 hours in an air-$CO_2$ (95/5%) atmosphere.

At the end of the trial, the total cellular proteins are assayed by the Coomassie blue method. This test consists, first of all, in rinsing the cells with PBS at the end of the treatment. A solution of NaOH (50 µl) is then added to each well. After 10 minutes of incubation, 200 µl of a dilute Biorad solution is added to each of the wells. The absorbance of the solutions at 570 nanometers is then measured after five minutes of incubation. A calibration series is constructed in parallel with the aid of BSA (Bovine Serum Albumin) which makes it possible to convert the optical densities obtained to microgram equivalents of proteins per well.

Various concentrations of walnut cake extract were thus tested, respectively 0.1 mg/ml and 0.25 mg/ml, in the suboptimum medium. A suboptimum control batch and an optimum control batch were also produced.

The proteins were assayed at $D_0$ and at $D_3$. The results are reproduced in the table below.

|  | Proteins (µg/well) | |
|---|---|---|
|  | $D_0$ | $D_3$ |
| Optimum control | 3.04 | 17.70 |
| Suboptimum control | 3.04 | 13.93 |
| Concentration 0.1 mg/ml | 3.04 | 19.81 |
| Concentration 0.25 mg/ml | 3.04 | 19.33 |

A very marked increase in the mass of cellular proteins is observed in the keratinocytes treated with the extract of the invention.

Accordingly, the extract of the invention therefore indeed has a stimulatory effect on cellular metabolism, that is to say protein synthesis in the keratinocytes.

c) Study on Fibroblasts

The effects of the extract of the invention on the incorporation of leucine into various protein fractions newly synthesized by human fibroblasts in monolayer culture were studied in this test.

After culture of the human skin fibroblasts until the cells become confluent, the culture medium is replaced by a medium containing 2% FCS (Fetal Calf Serum) with:

either the extract of the invention at 4 different concentrations, respectively 0.25 mg/ml, 0.1 mg/ml, 0.05 mg/ml and 0.01 mg/ml;

or vitamin C (reference product).

A batch of untreated control culture is performed in parallel.

After 24 hours of incubation at 37° C., labeled leucine ($^3$H-leucine) is added to the culture medium and the medium is left to incubate for an additional 48 hours. The following are recovered separately:

on the one hand, the culture medium, on the other hand, the cell lysate after cellular lysis, and finally the insoluble fraction (membranes, matrix deposited).

The macromolecules are extracted and then the incorporation of the radioactive precursor of these molecules is measured by liquid scintillation.

The results are presented in the table below.

Macromolecules extracted from the culture medium

| Treatment | Counts/minute | % Control | P (significance) |
|---|---|---|---|
| Control | 26257 ± 3567 | 100 | — |
| Vitamin C | 34748 ± 2599 | 132 | <0.05 |
| Extract of the invention | | | |
| 0.25 mg/ml | 34088 ± 1971 | 130 | <0.05 |
| 0.1 mg/ml | 32572 ± 4184 | 124 | >0.05 |
| 0.05 mg/ml | 28512 ± 2771 | 109 | >0.05 |
| 0.01 mg/ml | 27664 ± 2519 | 105 | >0.05 |

Macromolecules extracted from the intracellular medium

| Treatment | Counts/minute | % Control | P (significance) |
|---|---|---|---|
| Control | 37298 ± 2213 | 100 | — |
| Vitamin C | 35953 ± 4349 | 96 | >0.05 |
| Extract of the invention | | | |
| 0.25 mg/ml | 42786 ± 5990 | 115 | >0.05 |
| 0.1 mg/ml | 43571 ± 3921 | 117 | >0.05 |
| 0.05 mg/ml | 41530 ± 2844 | 111 | >0.05 |
| 0.01 mg/ml | 45199 ± 1675 | 121 | >0.05 |

Insoluble fraction (matrix, membranes)

| Treatment | Counts/minute | % Control | P (significance) |
|---|---|---|---|
| Control | 50372 ± 7511 | 100 | — |
| Vitamin C | 56865 ± 3853 | 113 | >0.05 |
| Extract of the invention | | | |
| 0.25 mg/ml | 65854 ± 5154 | 131 | <0.01 |
| 0.1 mg/ml | 64060 ± 983 | 127 | <0.05 |
| 0.05 mg/ml | 54621 ± 5542 | 108 | >0.05 |
| 0.01 mg/ml | 56352 ± 86 | 112 | >0.05 |

Total

| Treatment | Counts/minute | % Control | P (significance) |
|---|---|---|---|
| Control | 113928 ± 12162 | 100 | — |
| Vitamin C | 127566 ± 10289 | 112 | >0.05 |
| Extract of the invention | | | |
| 0.25 mg/ml | 142737 ± 5090 | 125 | <0.01 |
| 0.1 mg/ml | 140204 ± 8253 | 123 | <0.01 |
| 0.05 mg/ml | 124663 ± 7706 | 109 | >0.05 |
| 0.01 mg/ml | 129216 ± 2953 | 113 | >0.05 |

It is observed that the extract, at a concentration of 0.25 mg/ml, significantly stimulated the incorporation of leucine into the soluble secreted protein, fraction (identical to the reference product vitamin C).

It is also observed that, at a concentration of 0.1 mg/ml, the extract still stimulates the incorporation of leucine into this fraction.

Likewise, the stimulatory activity of the extract of the invention at 0.25 mg/ml and 0.1 mg/ml was observed in the insoluble protein fraction.

On the other hand, it is noted that the extract of the invention does not significantly modify the incorporation of leucine into the soluble cellular fraction, which confirms that the extract does not stimulate the multiplication of fibroblasts in culture.

In conclusion, as the extract of the invention stimulates the incorporation of leucine by the fibroblasts, it can be deduced therefrom that the extract significantly increases the synthesis of proteins and more specifically the proteins secreted by the fibroblasts, namely the proteins of the extracellular matrix (collagens, glycosaminoglycans, and the like).

Anti Elastase Activity of the Extract of the Invention

This activity is evaluated on cellular extracts of fibroblasts of human dermis, isolated from the foreskin and cultured according to routine techniques at 37° C., in a humid air-$CO_2$ (95/5%) atmosphere.

The fibroblasts are cultured in DMEM medium supplemented with fetal calf serum (10% FCS) and passaged regularly until a sufficient biomass is obtained.

To carry out the test, the cells are detached from their support by trypsinization. After centrifugation and suitable treatment, the cellular extracts are recovered.

The elastase activity of the cellular extracts was evaluated using Suc-(L-Ala)$_3$-p-nitroanilide (SANA) as substrate. Aliquots of the cellular extract are preincubated at 37° C. in TEA (triethanolamine) buffer at pH=7.8, alone or in buffer containing various concentrations of extracts.

After incubation, a solution of SANA is added to the reaction mixture. The catalytic activity of the cellular extract is assessed by measuring the level of release of p-nitroanilide, which exhibits a maximum absorption at 405 nm.

The optical densities at 405 nm are recorded for 1 hour 30 min to 2 hours.

The effects of the extract of the invention on the elastase activity were studied for five different concentrations, respectively 0.5 mg/ml, 1 mg/ml, 2 mg/ml, 5 mg/ml and 10 mg/ml. A positive control was introduced into the trial (dichloroisocoumarin at 2 mM).

The results are grouped together in the following table.

| | Control | 0.5 | 1 | 2 | 5 | 10 | DCI |
|---|---|---|---|---|---|---|---|
| mU elastase/$10^6$ cell | 0.682 | 0.577 | 0.503 | 0.424 | 0.332 | 0.310 | 0.431 |
| Inhibition | — | 15.3 | 26.3 | 37.7 | 51.4 | 54.7 | 37 |

The results obtained show that the extract of the invention is capable of inhibiting the elastase activity in a dose-dependent manner.

Under the selected experimental conditions, the median inhibitory concentration of the extract was evaluated at 5.6 mg/ml.

Anti Collagenase Activity of the Extract of the Invention

The effect of the extract of the invention on the anti collagenase activity was studied.

This activity was evaluated by the fluorescamine method.

The test is based on the formation of fluorescent compounds between fluorescamine and primary amines, amino acids and peptides. In practice, the increase in the fluorescence emission obtained after incubation of a solution of collagen type I and of collagenase in the presence of fluorescamine is measured.

The evaluation of the catalytic activity of the collagenase is carried out in the absence or in the presence of various concentrations of the extract, respectively for 0.5 mg/ml, 1 mg/ml, 2 mg/ml, 5 mg/ml and 10 mg/ml.

The results are reproduced in the table below.

| Concentration mg/ml | Inhibition |
| --- | --- |
| 0.5 | 6.4% |
| 1 | 6.6% |
| 2 | 12.6% |
| 5 | 19.5% |
| 10 | 17.2% |

As the results show, an inhibitory effect is observed on the collagenase activity.

As already stated, the invention also relates to a cosmetic composition comprising a walnut seed cake extract as described above.

To obtain a cosmetic composition exhibiting the abovementioned properties, the cake extract of the invention is used in the form of a solution having a concentration of between 10 and 40 grams of dry matter per liter of solvent, advantageously 30 g/l.

In practice, the composition contains between 0.5 and 10%, advantageously between 2 and 5%, by weight of the abovementioned solution of extract of the invention of walnut seed cake. Of course, the extract will be incorporated into the cosmetic composition with any customary formulation excipient.

The cosmetic composition may be provided in particular in the form of a cream, a milk, a gel, sera, microemulsions and the like.

As already stated, this composition may be used in cosmetics for the treatment of skin ageing or alternatively as agent for protecting the skin against environmental stress induced in particular by UV radiation.

The invention finally relates to a method of cosmetic treatment for combating skin ageing, characterized in that it consists in applying to the skin an effective quantity of the cosmetic composition described above.

The advantages of the invention will emerge more clearly from the exemplary embodiments which follow.

EXAMPLE 1

Formulation of a Protective Cream Based on the Extract of the Invention

The following five phases are prepared:

| | |
| --- | --- |
| Phase I | |
| Plurol ® stearic | 5% |
| Cetyl alcohol | 2% |
| Octyldodecyl myristate | 3% |
| Lipophilic Labrafac ® WL 1349 | 3% |
| Ceraphyl 368 | 4% |
| Dimethicone | 5% |
| Camellia oil | 3% |
| Phenonip | 0.5% |
| Phase II | |
| Demineralized water | 35% |
| Avicel RC 591 | 1% |
| Phase III | |
| Demineralized water | qs |
| Ultrez 10 | 0.15% |
| Sodium hydroxide (10% solution) | 0.3% |
| Phase IV | |
| Dow Corning 1403 | 2% |
| Phase V | |
| Solution of extract of the invention (30 g/l) | 3% |

The manufacture of the cream is carried out according to the following method.

The Avicel RC 591 is first of all dispersed in water. The Ultrez 10 is then sprinkled in water. The mixture is neutralized with sodium hydroxide. Phases II and III, previously heated to 55° C., are then added, with stirring, to phase I heated to 75° C. The mixture is cooled, with stirring, and, around 50° C., phase IV is added. Phase V is added, with stirring, at a temperature in the region of 35° C.

EXAMPLE 2

Formulation of an Anti Age Cream

| | |
| --- | --- |
| Phase I | |
| Apifil ® | 8% |
| MOD | 10% |
| ISIS | 10% |
| Phenonip | 0.6% |
| Phase II | |
| Demineralized water | qs |
| Carbopol 934 | 0.2% |
| Phase III | |
| Sodium hydroxide (10% solution) | 0.4% |
| Phase IV | |
| Transcutol ® CG | 5% |
| Solution of extract of the invention (30 g/l) | 5% |
| Perfume | qs |

The manufacture of the anti age cream is carried out according to the following method.

The Carbopol is first of all dispersed in phase II. Phase II, heated to 75° C., is then added, with stirring, to phase I, also heated to 75° C. Sodium hydroxide is added. Still with stirring, the mixture is cooled and, at a temperature in the region of 30° C., the other constituents are added.

EXAMPLE 3

Formulation of a Foam Gel for Sensitive Skins

| Phase I | |
| --- | --- |
| Oronal LCG | 20% |
| Oronal BLD | 20% |
| Amonyl 440 NI | 10% |
| Oramide DL 200 | 1.8% |
| Softcutol ® O | 1% |
| Phenonip | 0.5% |
| Perfume | 0.5% |
| Phase II | |
| Demineralized water | qs |
| Solution of extract of the invention (30 g/l) | 2% |
| Phase III | |
| Citric acid (50% solution) | 0.07% |

The manufacture of the foam gel is carried out according to the following method.

In the cold, all the constituents of phase I are mixed in the order of the formula. Phases II and III are then added, with slow stirring.

EXAMPLE 4

Formulation of an After-sun Milk

| Phase I | |
| --- | --- |
| Tefose ® 2000 | 7% |
| Cetyl alcohol | 2% |
| Geleol | 1% |
| ISIS | 5% |
| MOD | 5% |
| Dimethicone | 2% |
| Phase II | |
| Demineralized water | qs |
| Carbopol 941 | 0.1% |
| Solution of extract of the invention (30 g/l) | 5% |
| Phase III | |
| Sodium hydroxide (10% solution) | 0.2% |
| Phase IV | |
| Perfume | 0.2% |
| Germaben II | 1% |

The after-sun milk is manufactured according to the following method.

The Carbopol is first of all dispersed in water. Phase II, heated to 75° C., is then added, with stirring, to phase I, heated to the same temperature. The sodium hydroxide solution is then incorporated. Finally, still with stirring, the mixture is cooled to a temperature in the region of 30° C. and the other constituents are added.

The advantages of the invention emerge clearly from the description. The capacity of the walnut seed cake extract to stimulate protein synthesis, in particular in cells of the dermis and of the epidermis, so as to act against skin ageing, will be noted in particular. Its anti-inflammatory activity and its protective activity toward "environmental stress" and in particular UV radiation, generating cumulative deleterious effects is also noted.

These different applications make walnut seed cake extract a complete active agent intended for combating not only intrinsic ageing by stimulating cellular metabolism, but also extrinsic ageing through its protective activity.

What is claimed is:

1. A walnut seed cake extract produced by the process of:
    (a) bringing walnut seed cake into contact with water, whereby an aqueous solution and a water-insoluble residue are produced;
    (b) separating the aqueous solution from the residue; and
    (c) removing at least a portion of water from said aqueous solution.

2. A walnut seed cake extract according to claim 1 produced by the process of:
    (a) bringing walnut seed cake into contact with four to 99 parts by weight of water at 3° C. to 100° C. for a period of one minute to forty hours, whereby said aqueous solution and said water-insoluble residue are produced.

3. A walnut seed cake extract according to claim 1 produced by the process of:
    (a) macerating walnut seed cake in about 19 parts by weight of water at 3° C. to 10° C. for about 20 hours to produce said aqueous solution and said residue.

4. A walnut seed cake extract as claimed in claim 1, wherein the removal of water is carried out by reverse osmosis.

5. A walnut seed cake extract as claimed in claim 3 wherein the maceration is carried out at about 4° C.

6. A walnut seed cake extract as claimed in claim 1, wherein removal of water is carried to substantial completion, resulting in a powder.

7. A walnut seed cake extract as claimed in claim 1, wherein the walnut seed cake is derived from the seed of *Juglans regia*.

8. A method for therapeutic or prophylactic treatment of skin cells comprising applying to said skin cells the walnut seed cake extract of claim 1.

9. A method according to claim 8 for protecting skin cells against oxidative stress induced by UVB radiation comprising applying said walnut seed cake to said skin cells.

10. A method according to claim 8 for inhibiting inflammation in skin cells comprising applying said walnut seed cake to said skin cells.

11. A method according to claim 8 for retarding ageing in skin cells comprising applying said walnut seed cake to said skin cells.

12. A method according to claim 8 for stimulating the synthesis of proteins by cells of the dermis and epidermis comprising applying said walnut seed cake to said cells.

13. A method according to claim 8 for stimulating the synthesis of glycosaminoglycans by cells of the dermis comprising applying said walnut seed cake to said cells.

14. A method according to claim 8 for inhibiting collagenase in skin cells comprising applying said walnut seed cake to said skin cells.

15. A method according to claim 8 for inhibiting elastase in skin cells comprising applying said walnut seed cake to said skin cells.

16. A method according to claim 8 for inhibiting apoptosis in skin cells comprising applying said walnut seed cake to said skin cells.

17. A cosmetic composition comprising the walnut seed cake extract of claim 1 and a pharmaceutically acceptable vehicle for topical administration.

18. The cosmetic composition as claimed in claim 17, wherein said walnut seed extract is in the form of a solution having a concentration of between 10 and 40 g of dry matter per liter of solvent.

19. The cosmetic composition as claimed in claim 18, characterized in that it contains between 0.5 and 10% by weight of said solution.

20. A cosmetic composition comprising
   (1) from 90 to 99.5% by weight of a pharmaceutically acceptable vehicle for topical administration and
   (2) from 0.5 to 10% by weight of a walnut seed cake extract produced by the process of:
   (a) macerating walnut seed cake in water at 3° C. to 10° C. to produce an aqueous solution and a residue;
   (b) separating the aqueous solution from the residue; and
   (c) removing at least a portion of water from said aqueous solution to provide a solution having a concentration of between 10 and 40 g of dry matter per liter of solvent.

21. The cosmetic composition as claimed in claim 20, wherein said solution has a concentration of about 30 g of dry matter per liter of solvent and said solution constitutes between 2 and 5% by weight of said composition.

22. A method of cosmetic treatment wherein a therapeutically effective quantity of the cosmetic composition as claimed in claim 17 is applied to the skin.

23. A method of cosmetic treatment wherein a therapeutically effective quantity of the cosmetic composition as claimed in claim 20 is applied to the skin.

* * * * *